United States Patent [19]

Eyal et al.

[11] Patent Number: 5,155,038
[45] Date of Patent: Oct. 13, 1992

[54] USE OF THROMBOSPONDIN TO PROMOTE WOUND HEALING

[75] Inventors: Jacob Eyal, Baltimore, Md.; George Tuszynski, Mays Landing, N.J.

[73] Assignees: W. R. Grace & Co.-Conn., New York, N.Y.; Medical College of Pennsylvania, Philadelphia, Pa.

[21] Appl. No.: 483,500

[22] Filed: Feb. 22, 1990

[51] Int. Cl.$^5$ .......................... C12P 21/02; C12N 5/00; A01N 25/24; A61K 37/10
[52] U.S. Cl. ........................... 435/240.2; 514/8; 435/70.21; 424/77
[58] Field of Search .............. 514/8; 435/70.21, 240.2; 424/77

[56] References Cited

U.S. PATENT DOCUMENTS 4,578,079  3/1986  Ruoslahti .
4,614,517  9/1986  Ruoslhati .
4,792,525  12/1988  Ruoslahti .

OTHER PUBLICATIONS

Grinnell (1982) The American Journal of Dermatopathology vol. 4, No. 2, pp. 185–188.
Varani et al. (1988) J. Clin. Invest. vol. 81 pp. 1537–1544.
Alexander et al. Biochem. J. 217:67–71 1984.
Asch et al. Proc. Ntl. Acad. Sci. 83:2904–8 1986.
Clezardlin et al. J. Chromatog. 296:249–56 1984.
Dixit et al. Proc. Ntl. Acad. Sci. 83:5449–53 1986.
Hennessey et al. J. Cell Biol. 108:729–36 1989.
Kobayashi et al. Biochemistry 25:8418–25 1986.
Lahav et al. Eur. J. Biochem. 145:151–6 1984.
Lawler J. Biol. Chem. 253:8609–16 1978.
Lawler et al. Thromb. Res. 22:267–9 1981.
Lawler et al. J. Biol. Chem. 103:1635–48 1986.
Leung J. Clin. Invest. 74:1764–72 1986.
Majack et al. J. Biol. Chem. 101:1059–70 1985.
Majack et al. Proc. Ntl. Acad. Sci. 83:9050–4 1986.
Majack et al. Cell Membrane 3:57–77 1987.
Majack et al. J. Biol. Chem. 262:8821–5 1987.
Majack et al. J. Biol. Chem. 106:415–22 1988.
Raugi et al. J. Invest. Dermatol. 39:551–4 1987.
Santoro Sem. In Thromb. and Hemo. 13:290–7 1987.
Tashiro et al. J. Biol. Chem. 264:16176–82 1989.
Tuszynski et al. J. Bio. Chem. 260:12240–5 1985.
Tuszynski et al. Sem. in Thromb. and Hemo. 13:361–8 1987.
Wikner et al. J. Invest. Dermatol. 88:207–11 1987.

Primary Examiner—David L. Lacey
Assistant Examiner—Gian P. Wang
Attorney, Agent, or Firm—Vanessa L. Appleby; Jill H. Krafte; Steven T. Trinker

[57] ABSTRACT

Pharmaceutical compositions and dressings useful in wound healing are provided. The pharmaceutical compositions comprise thrombospondin as the active ingredient.

4 Claims, No Drawings

USE OF THROMBOSPONDIN TO PROMOTE WOUND HEALING

TECHNICAL FIELD

This invention relates to the field of wound healing. More specifically it relates to the ability of thrombospondin and its derivatives to improve wound healing and to increase the rate at which wounds heal.

BACKGROUND

Wound healing in humans and other mammals is often inadequate and incomplete. Delayed healing markedly increases hospitalization costs, and often the wound continues as a chronic sore that requires extensive attention and medical care in order to control infection and tissue necrosis. Even when such wounds finally heal, the "wound area" is often devoid of the ability to respond to tactile stimulus, and is often filled with excessive deposits of collagen that lead to permanent scarring. The need for improved wound healing also extends to wounds generated by surgical procedures. For instance, although cosmetic surgery is one of the fastest growing medical specialty areas, the success of such procedures is limited by the adequacy of healing in the typically adult and elderly clientele. Further, hair transplants often fail due to an inadequate blood supply around the transplant. Enhanced healing and neovascularization of the transplant would enhance the establishment of the graft.

The rapidity of reestablishment of a biological coverage on wound surfaces is a critical element in the healing prognosis. Natural open wounds are first covered by a blood and plasma exudate which dries to form the initial "scab" that covers the wound. This scabby layer forms a short-term protective coverage from outside elements while healing proceeds under this layer.

For longer-term coverage of extensive wounds, surgeons often resort to transplants in which a thin piece of superficial skin (called a "split-thickness skin graft") is implanted over the wound to form an island of skin cells that can overgrow the surface. Deeper skin wounds often require a more extensive skin transplant (called a "full-thickness skin flap") in which the entire skin down to the muscular layers is moved to cover the wounds. Split-thickness flaps are hampered by the low degree of surgical "take." Typically, only about 20% to 40% of the transplanted skin successfully reestablishes itself in its new position. Full-thickness flaps are even more difficult to reestablish in a new site. Surgeons are usually constrained to leave one end of the flap attached to a blood supply, while the other end is stretched to the new site to be sewn in place. Only after the transplanted end of the flap reestablishes a new blood supply is the other end of the flap moved to the new site to complete the transplant. Such procedures often result in extensive loss of tissue and additional pain and suffering for the patient.

Wound healing can be divided into four essential components: inflammation, angiogenesis, collagen deposition and epithelialization. All of these play a role in the healing of all wounds.

In recent years, a number of protein factors have been shown or implicated to be useful in wound healing. These factors are essential to the growth and differentiation of the cells which serve to replace the tissue destroyed. A number of candidate factors have been identified on the basis of the ability of extracts from various tissues, such as brain, platelets, pituitary, and hypothalamus, to stimulate the mitosis of cultured cell lines. These factors include transforming growth factors (TGF), fibroblast growth factor (FGF), platelet derived growth factor (PDGF), insulin-like growth factors (IGF), epidermal growth factor (EGF), and a myriad of other proteins. This invention shows that thrombospondin has now been identified as an alternative protein which may be used in a similar fashion to promote wound healing.

Thrombospondin (also known as thrombin sensitive protein or TSP) is a large molecular weight 180 kD glycoprotein composed of three identical disulfide-linked polypeptide chains. TSP is stored in the alpha-granules of platelets and secreted by a variety of mesenchymal and epithelial cells (Majack et al., *Cell Membrane* (1987)3:57-77). Platelets secrete TSP when activated in the blood by such physiological agonists such as thrombin. TSP has lectin properties and has a broad function in the regulation of fibrinolysis and as a component of the extracellular matrix (ECM). TSP is one of a group of ECM proteins which have adhesive properties. Other ECM proteins include laminin, fibronectin and fibrinogen. TSP binds to fibronectin and fibrinogen (Lahav, et al., *Eur. J. Biochem.* (1984) 145:151-6) and these proteins are known to be involved in platelet adhesion to substratum and platelet aggregation (Leung, *J. Clin. Invest* (1986) 74:1764-1772).

Lawler (*J. Biol. Chem.* (1978) 253:8609-16) first described the purification of TSP from the alpha granules of activated platelets using exclusion chromatography. TSP has subsequently been purified by heparin affinity chromatography (Lawler et al., *Thromb Res* (1981) 22:267-269), fibrinogen affinity chromatography (Tuszynski et al., *J. Biol. Chem.* (1985) 260:12240-5), barium chloride precipitation (Alexander et al., *Biochem. J.* (1984) 217:67-71) and anion exchange chromatography with HPLC (Clezardlin et al., *J. Chromatog.* (1984) 296:249-56).

The complete amino acid sequence of TSP has been deduced from DNA clones prepared by various groups including Lawler et al., *J. Cell Biol.* (1986) 103:1635-48, Kobayashi et al., *Biochemistry* (1986) 25:8418-25, Dixit et al., *Proc. Ntl. Acad. Sci.* (1986) 83:5449-53 and Hennessy et al., *J. Cell Biol.* (1989)108:729-36.

Work from several laboratories has implicated TSP in response of cells to growth factors. Submitogenic doses of PDGF induce a rapid but transitory, increase in TSP synthesis and secretion by rat aortic smooth muscle cells. (Majack et al., *J. Biol. Chem.* (1985) 101:1059-70). PDGF responsiveness to TSP synthesis in glial cells has also been shown. (Asch et al., *Proc. Ntl. Acad. Sci.* (1986) 83:2904-8). TSP mRNA levels rise rapidly in response to PDGF (Majack et al., *J. Biol. Chem.* (1987) 262:8821-5). TSP acts synergistically with epidermal growth factor to increase DNA synthesis in smooth muscle cells (Majack et al., *Proc. Ntl Acad Sci* (1986) 83:9050-4) and monoclonal antibodies to TSP inhibit smooth muscle cell proliferation (Majack et al., *J. Biol Chem* (1988) 106:415-22). TSP modulates local adhesions in endothelial cells.

The TSP protein sequence includes the X-RGD-Y sequence first described by Ruoslahti (U.S. Pat. No. 4,578,079, U.S. Pat. No. 4,614,517 and U.S. Pat. No. 4,792,525). Ruoslahti discloses that the RGD sequence is believed to confer adhesive properties. However, other distinct non-RGD peptides have been identified in proteins which contain the RGD sequence elsewhere, and those non-RGD peptides have also been shown to confer adhesive properties (Tashiro et al., *J. Biol. Chem.* (1989) 264:16176–82).

Varani et al. (*J. Clin. Invest.* (1988) 81:1537–1544) shows that TSP has an effect on the differentiation of human epidermal keratinocytes and suggests that TSP may participate in reepithelialization during wound repair.

Immunostaining studies have indicated that TSP may be present in the extracellular matrix of wounds (Raugi et al., *J. Invest. Dermatol.* (1987) 39:551–554). However, the mere presence of TSP in a wound does not demonstrate its use in healing wounds.

The use of TSP or its derivatives has never before been shown to improve wound healing or to increase the rate at which wounds heal.

SUMMARY OF THE INVENTION

This invention provides methods for using thrombospondin to enhance and promote wound healing in mammals, preferably humans. In other aspects, the invention relates to TSP-containing compositions such as pharmaceutical compositions and wound dressings.

DETAILED DESCRIPTION OF THE INVENTION

As indicated above, the present invention provides methods, pharmaceutical compositions, and wound dressings which use thrombospondin or its derivatives to enhance or promote wound healing in mammals, preferably humans.

A. Definitions

"Thrombospondin" is defined herein as a three chain glycoprotein composed of identical disulfide linked polypeptide chains that migrate on discontinuous SDS gels with apparent molecular weights of 180,000 (Lawler et al., *J. Biol. Chem.* (1986) 103:1635–48). Nondenatured thrombospondin has a molecular weight of 420,000 as shown by equilbrium sedimentation analysis & can be described as a prolate ellipsoid with an axial ratio of 9.3 (Margossian et al., *J. Cell Chem.* (1981) 256:7495–7500). Thrombospondin is represented by the amino acid sequence described in Lawler et al (supra). Of course, this definition is not restricted to the specific sequence shown in Lawler et al., but includes proteins which contain accidentally or deliberately induced alterations, such as deletions, additions, or exchanges of amino acid residues, so long as the biological activity does not change.

"Derivatives" is defined herein as fragments, extensions or modifications of the thrombospondin molecule which retain biological activity.

The thrombospondin, of this invention, and its derivatives, can be isolated from natural sources, produced recombinantly or produced synthetically by solid phase procedures.

B. Administration and Use

Purified protein factors are generally applied topically to the traumatized tissue in order to stimulate vascularization and healing. Appropriate substrates are burns, wounds, bone fractures, surgical abrasions such as those of plastic surgery, or others requiring repair. Because application of protein factors accelerates healing, the risk of infection is reduced.

Indications wherein TSP or its derivatives is of value in encouraging neovascularization include skin conditions such as burns, cuts, lacerations, bed sores, and slow-healing ulcers such as those seen in diabetics; musculo-skeletal conditions such as bone fractures, ligament and tendon repair, tendonitis, and bursitis; and in tissue repair during ischaemia and myocardial infarction.

Formulations of TSP or its derivatives using available excipients and carriers are prepared according to standard methods known to those in the art. The TSP can be formulated as lotions, gels, ointments, or as part of a controlled slow-release system. TSP can be formulated with additional active ingredients, such as antibiotics, if desired.

It is expected that TSP may act in concert, and even synergistically, with other growth factors such as fibroblast growth factor (FGF), epidermal growth factor (EGF), the transforming growth factors (TGF), insulin-like growth factors (IGF-1 and IGF-2), and/or platelet-derived growth factor (PDGF). Therefore, also included within the formulations, compositions and administration protocols of the invention are embodiments wherein the TSP of the invention is administered in the same composition with, or in the same protocol with, one or more of the foregoing factors, thus more effectively to achieve the desired tissue repair.

For topical administration, which is the most appropriate with regard to superficial lesions, standard topical formulations are employed using, for example, 0.001–10% solutions, preferably 0.01–1% solutions. Such solutions would be applied 3–6 times a day to the affected area. The concentration of the ointment or other formulation depends, of course, on the severity of the wound. In most protocols, the dose may be lowered with time to lessen likelihood of scarring. For example, the most severe wounds, such as third degree burns, preferably are treated with a 1.0% composition, but as healing begins, the dose may be progressively dropped to approximately 0.01% or lower.

For bone and tissue repair, local administration is preferred, which can be accomplished by means of subcutaneous implant or slow release formulation implanted directly proximal to the target. Surgery may be required for such conditions as bone injuries, thus making implantation directly practical. Slow-release formulations are prepared according to standard methods known to those in the art. Slow-release forms can be formulated in polymers, such as Hydron TM polymer, (Langer et al., *Nature* (1976) 263:797–799) or Elvax 40P TM polymer (DuPont) (Murray et al., *In Vitro* (1983) 19:743–747). Other sustained-release systems have been suggested by Hsieh et al., *J. Pharm. Sci.* (1983) 72:17–22). TSP-containing formulations can be prepared with these systems as well.

As with topical administration, for sustained-release delivery, the concentration of TSP in the formulation depends on a number of factors, including the severity of the condition and the rate of TSP release from the polymer. In general, the formulations are constructed so as to achieve a constant local concentration of about 100 times the normal tissue concentration, as described by Buckley et al. (*Proc. Natl. Acad. Sci.* USA (supra)). The initial concentration, of course, depends on the severity of the wound.

TSP protein is particularly useful, also, in aiding the reformation and repair of tissues traumatized during surgery. For this use, it may be desired to embed the TSP protein in polymers used to coat surgical staples. The protein thus is able to supplement biologically the mechanical suturing effected by the staples, and to augment and abet the "natural" healing processes in the repaired tissues.

In addition, it has been shown that angiogenic stimuli, such as those provided by TSP, result in the release of tissue plasminogen activator (tPA) and of collagenase in vitro (Gross et al., *Proc. Natl. Acad. Sci.* (1983) 80:2623-2627). Therefore, the TSP protein of the invention is also useful in treatment of conditions which respond to these enzymes. While it may be necessary in acute situations (such as the presence of a blood clot associated with stroke or heart attack) to directly administer large doses of tPA to dissolve the clot, for treatment of chronic propensity to form embolisms, systemic administration of TSP to maintain a suitable level of tPA in the blood stream may be desirable. For this indication, systemic administration of the TSP, using conventional means such as intramuscular or intravenous injection, is preferred.

The following abbreviations have been used throughout in describing the invention.
cm—centimeter
ECM—extracellular matrix
EGF—epidermal growth factor
FGF—fibroblast growth factor
g—gram
H&E—hematoxylin and eosin
IGF—insulin-like growth factor
µg—microgram
ml—milliliter
NBF—neutral buffered formalin
ng—nanogram
PDGF—platelet derived growth factor
%—percent
TGF—transforming growth factor
TSP—thrombospondin The following examples are intended to illustrate the invention, without acting as a limitation on its scope.

EXAMPLES

Human Platelet Thrombospondin was tested in the state-of-the-art in vivo wound healing model—full thickness wounds in pigs. This model is used to determine enhancement/promotion of epithelial cell growth in the wound during the first days of the healing process.

Two healthy Yorkshire pigs were used in this study. The pigs were fed commercial pig starter ration and given tap water ad libitum throughout the study. Husbandry was conducted in accordance with the "Guide for the Care and Use of Laboratory Animals," NIH Publication No. 85-23. On the day before the treatment, each pig was weighed. Body weights were 16.5 and 13.1 kg respectively.

At the time of treatment, each pig was given a combination of ketamine HCl and acepromazine maleate by intramuscular injection and was then placed on halothane/oxygen inhalation. The surgical area was washed with povidone iodine soap and rinsed with sterile 0.9% sodium chloride solution. While under general anesthesis, full thickness skin wounds were made with a scalpel. Three wounds measuring approximately 1.5 cm×1.5 cm were created on each side (six total). Wounds were approximately 15 cm apart and 5 to 8 cm from the dorsal midline.

Immediately after wounding, each wound was individually covered with control dressing (Sof-Kling TM dressing). The Sof-Kling TM dressing covered wounds were then saturated with TSP protein in phosphate buffered saline (PBS) solution, PBS only or nothing. TSP was purified using the procedure of Tuszynski et al. (*J. Biol. Chem.* (1985) 260:12240-5) and was electrophoretically pure as judged by silver-stained SDS-gels. Rolled rubber dental dam was wrapped around the trunk of each pig to retard evaporation and to secure and protect the dressings; Ace bandages were wrapped around the animal over the rubber dam. Animals were returned to their cages and observed during recovery.

The pigs were observed individually each day for general condition and well being. At two, four, six, and eight days after wounding, each pig was again placed under general anesthesia. Dressings were removed and the wounds were examined. Wounds were gently debrided and/or flushed with sterile 0.9% sodium chloride solution if needed. Each skin defect was measured on each side and diagonally with a Draper caliper. The surface area of the defect was calculated. The skin around each wound was carefully wiped with alcohol and dried prior to treating or covering with the same material. The rolled rubber dental dam and Ace bandage were again placed on each pig. Pig number 2 developed a rectal probates on day nine and was humanely sacrificed. Pig number 1 was continued to 13 days.

According to these measurements and visual observation, TSP-treated wounds appeared to heal at a faster rate in some cases, particularly at 20 µg/ml dose, than the control dressing or PBS. All wounds (TSP treated and controls) healed during the course of the study, therefore TSP is not detrimental to the healing process.

Immediately after completion of wound observations and measurement (day 9 for pig #2, day 13 for pig #1) the pigs were humanely sacrificed. Each wound site was removed along with surrounding normal skin identified by dressing type and animal, and placed into 10% neutral buffered formalin (NBF). After fixation, the sites were trimmed and representative tissues from all sites were routinely processed, embedded, cut and stained in hematoxylin and eosin (H&E). Slides were submitted for microscopic evaluation by a board certified pathologist.

Microscopic evaluation revealed that treatment with TSP did not interfere with the wound healing process and all wounds showed similar changes. Pig #2 was sick from causes unrelated to the experiment (rectal probates) and showed more evidence of inflamation and no evidence of re-epithelialization. Healthy pig #1 showed re-epithelialization of various degrees in all wounds, the greatest degree being at 20 µg/ml.

What is claimed is:

1. A method for enhancing wound healing comprising administering to a wound in mammals a therapeutically effective amount of thrombospondin or thrombospondin derivative which retains biological activity to enhance wound healing in mammals.

2. The method of claim 1 wherein said thrombospondin or thrombospondin derivative is applied topically to the wound.

3. The method of claim 1 wherein said wound is a burn, cut, laceration, bed sore, slow-healing ulcer, or bone fracture.

4. A method of enhancing reepithelialization of wound tissue comprising administering to a wound in mammals a therapeutically effective amount of thrombospondin or thrombospondin derivative which retains biological activity to enhance wound healing in mammals.

* * * * *